United States Patent
Yamashita et al.

[11] Patent Number: 5,472,590
[45] Date of Patent: Dec. 5, 1995

[54] ION SENSOR

[75] Inventors: Koutarou Yamashita, Kokubunji; Mamoru Taki, Ibaraki; Yuji Miyahara, Kodaira; Toshiko Fujii, Kokubunji; Satoshi Ozawa, Mitaka; Yoshio Watanabe, Kokubunji, all of Japan

[73] Assignee: Hitachi, Ltd., Tokyo, Japan

[21] Appl. No.: 354,643

[22] Filed: Dec. 13, 1994

[30] Foreign Application Priority Data

Dec. 15, 1993 [JP] Japan .................................. 5-315080
Dec. 15, 1993 [JP] Japan .................................. 5-315081

[51] Int. Cl.$^6$ ................................................ G01N 27/26
[52] U.S. Cl. ................... 204/418; 204/419; 204/403; 204/409; 204/415; 422/82.03
[58] Field of Search .................................. 204/415, 418, 204/419, 416, 403, 409; 422/82.03

[56] References Cited

U.S. PATENT DOCUMENTS

| | | |
|---|---|---|
| 4,214,948 | 7/1980 | Battaglia et al. . |
| 4,409,980 | 10/1983 | Yano et al. . |
| 4,739,380 | 4/1988 | Lauks et al. . |
| 4,776,944 | 10/1988 | Janata et al. .................... 204/418 |
| 5,133,856 | 7/1992 | Yamaguchi et al. .............. 204/418 |
| 5,308,468 | 5/1994 | Katoh et al. ..................... 204/418 |
| 5,336,388 | 8/1994 | Leader et al. .................... 204/419 |
| 5,401,377 | 3/1995 | Shieh et al. ...................... 204/418 |

FOREIGN PATENT DOCUMENTS

| | | | |
|---|---|---|---|
| 2352300 | 5/1977 | European Pat. Off. | G01N 27/16 |
| 258951 | 9/1987 | European Pat. Off. | G01N 27/00 |
| 325562 | 1/1989 | European Pat. Off. | C01N 27/28 |
| 411127 | 4/1989 | European Pat. Off. | G01N 27/30 |
| 631130 | 3/1994 | European Pat. Off. | G01N 27/33 |
| 2221730 | 3/1974 | France | G01N 27/30 |

*Primary Examiner*—John Niebling
*Assistant Examiner*—Bruce F. Bell
*Attorney, Agent, or Firm*—Antonelli, Terry, Stout & Kraus

[57] ABSTRACT

An ion sensor having an ion selectivity, which comprises an internal electrode of metal/metal salt, composed of an electroconductive layer of at least one metal and a layer of an insoluble salt of the metal in contact with the electroconductive layer, an ion selective membrane whose supporting membrane is composed of a hydrophobic polymer, and an intermediate layer capable of keeping water molecules, provided between the internal solid electrode and the ion selective membrane, where the organic compound having a water-keeping property is polymethylene glycol, polyethylene glycol or polypropylene glycol, each having a molecular weight of 200 to 600, and the inorganic compound having a water-keeping property is calcium chloride, gold chloride, magnesium perchlorate, magnesium fluoride or vanadium chloride dioxide, is suitable for analysis of specific ion species in a biological fluid with practically prolonged maintenance of properties of electrode.

30 Claims, 5 Drawing Sheets

ION SENSOR

BACKGROUND OF THE INVENTION a) Field of the Invention

The present invention relates to an ion sensor suitable for analysis of ion species contained in a biological liquid, and more particularly to an ion sensor suitable for analysis of potassium ion, sodium ion, halide ion or carbonate ion by potentiometric determination.

b) Related Art

The ion sensor can selectively determine concentrations of specific ion species in a solution and has been employed in various fields including concentration monitoring of specific ion species, water quality analysis, etc. Particularly in the medical field it is applied to quantitatively determine ion species in blood or biological liquids such as urine, etc., for example, chloride ions, potassium ions, etc. Since concentrations of specific ion species in a biological liquid are closely related to metabolic reactions of living bodies, hypertension symptom, kidney disorder, neurosis trouble, etc. are diagnosed by determining concentrations of specific ion species.

Between an activity a of ion species to be determined and an electrode potential level E given by an ion sensor, a correlation that the logarithm of activity a is proportional to a change in the level E is established as shown by the following equation:

$$E = E_0 + 2.303(RT/ZF) \log a$$

and the activity a of ion species to be determined can be simply calculated from measurements of the level E. In the foregoing equation, R is a gas constant, T an absolute temperature, Z an ionic factor, F a Faraday constant and $E_0$ a standard potential of the system. With the ion sensor, concentrations of ion species existing in blood or a biological liquid can be determined in a broad concentration range only by measuring the potential level.

Generally, an ion sensor comprises an internal solid electrode, an ion selective membrane, an internal solution, where an agar gel containing a supporting electrolyte is used as the inner solution serving to conduct electricity between the ion-selective membrane and the inner electrode. Among ion sensors, an ion sensor in such a structure that the ion selective membrane is directly provided on the internal solid electrode without using any internal solution is called coated wire electrode (CWE). CWE is simple in the electrode preparation, handling, maintenance, etc. and thus has been intensively studied.

Ion sensor disclosed in U.S. Pat. No. 4,214,968 can directly read concentrations of specific ion species as a function of ion activity by spotting a liquid sample without any preparative adjustment, storage by wet process or equilibration.

The above-mentioned CWE generally comprises an ion selective membrane, an internal solid electrode and an electrode body. Since the internal solid electrode is in direct contact with the ion selective membrane, the electrode potential level drifts largely and the electrode potential stability is not satisfactory when used for a prolonged time. Furthermore, the electrode resistance is high and CWE is highly susceptible particularly to changes in temperature.

The art disclosed in said U.S. Pat. No. 4,214,968 provides an ion sensor unnecessitating preparative adjustment, storage by wet process or equilibration, but is not suitable for continuous measurement of liquid samples flowing, for example, along a path and no mention is made of a suitable ion sensor for the continuous measurement at all.

SUMMARY OF THE INVENTION

An object of the present invention is to provide an ion sensor with practically prolonged maintenance of properties of electrode, freed from the above-mentioned problems of prior art.

According to the present invention, there is provided an ion sensor, which comprises an ion selective membrane (4a in FIG. 1), an internal solid electrode (2a in FIG. 1), a lead wire (11a in FIG. 1), a liquid sample path (5 in FIG. 1) and an electrode body (1 in FIG. 1), where an intermediate layer (3a in FIG. 1) is provided between the internal solid electrode and the ion selective membrane whose supporting membrane is composed of a hydrophobic polymer.

According to a first mode of the present invention, the intermediate layer comprises a hydrophilic polymer and an inorganic compound having a water-keeping property or an organic compound having a water-keeping property.

According to a second mode of the present invention, the intermediate layer comprises a hydrophilic polymer and one of pyridine, pyridazine, pyrazine, s-triazine, quinoline, isoquinoline, quinoxaline, acridine and a derivative thereof, or a hydrazine derivative represented by the following chemical formula:

where R and R' are hydrogen atoms, alkyl groups or hydrokyl groups and $n \geq 1$.

Furthermore, the present ion sensor having an ion selectivity comprises an internal solid electrode of metal/metal salt comprising an electroconductive layer of at least one metal and a layer of an insoluble salt of the metal in contact with the electroconductive layer, an ion selective membrane whose supporting membrane is comprises a hydrophobic polymer, and an intermediate layer capable of keeping water molecules provided between the internal solid electrode and the ion selective membrane, the intermediate layer being comprises dried residues of an aqueous solution of an inorganic compound having a water-keeping property, or an organic compound having a water-keeping property, a hydrophilic polymer and an inorganic salt, where the organic compound is selected from the group consisting of polymethylene glycol, polyethylene glycol and polypropylene glycol, each having a molecular weight of 200 to 600, and the inorganic compound is selected from the group consisting of calcium chloride, gold chloride, magnesium perchlorate, magnesium fluoride, and vanadium chloride dioxide.

According to the present invention, a plurality of the present ion sensors are provided along the path through which a liquid sample is made to flow, and the individual ion selective membranes of the ion sensors are brought into contact with the liquid sample to measure a plurality of ion species.

When a concentration of a specific ion species is to be measured by an ion sensor, an equilibrium potential is generally developed at the interface between the ion selective membrane whose supporting membrane is comprises of a hydrophobic polymer and the internal solid electrode. It seems that the equilibrium potential is generated mainly due to such a phenomenon that ionized metal ions from the internal solid electrode reach a distribution equilibrium at the interface between the hydrophobic ion selective membrane and the internal solid electrode. In the conventional ion sensor no satisfactory ionization takes place at the interface, and thus the distribution equilibrium is hardly reached.

The inorganic or organic compound having a water-keeping property used in the first mode of the present invention combines with water molecules on the basis of electrostatic interaction, thereby promoting ionic dissociation of inorganic salts from the intermediate layer due to the action of water molecules.

The compound used in the second mode of the present invention promotes ionization of the metal of the internal solid electrode on the basis of electrostatic interaction.

Thus, metal ions generated mostly by ionization of the metal of the internal solid electrode can rapidly reach at the interface between the ion selective membrane and the internal solid electrode, and thus an ion sensor with practically prolonged maintenance of properties of electrode can be provided. That is, liquid samples can be measured with a stable accuracy for a prolonged time in a path through which the liquid samples flow.

Thus, the present invention provides an ion sensor capable of serving for a prolonged time with an improved accuracy and a higher reliability.

PREFERRED EMBODIMENTS OF THE INVENTION

Figure 1:
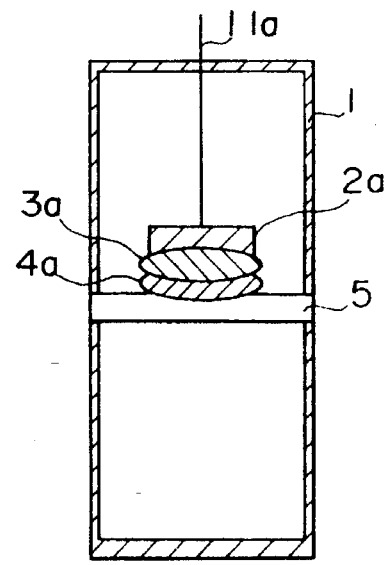
FIG. 1 is a vertical cross-sectional view showing the structure of a single ion sensor according to one embodiment of the present invention.

The present invention will be described in detail below, referring to embodiments and drawings.

Compounds applicable to embodiments of the present invention will be described below:

The term "water-keeping property" of a compound herein used means an ability of the compound to positively keep water molecules. That is, electrostatic bonding or some other bonding is established between the compound and water molecules on the basis of chemical or physical actions, and such a bonding can be maintained for a prolonged time.

Hydrophilic polymer for the intermediate layer is selected from the group consisting of poly(vinyl alcohol), polyethylene oxide, polypropylene oxide, polyacrylic acid salt, polymethacrylic acid salt, polystyrene acid salt, carboxylmethyl cellulose and a derivative thereof.

Compounds having a water-keeping property include deliquescent solids. Daliquescency appears mostly in inorganic compounds when the water vapor pressure of an aqueous saturated solution of a solid is lower than the partial pressure of water vapor in the air in contact with the aqueous saturated solution. In inorganic compounds, water molecules exist as water of crystallization. Water of crystallization is the water contained in a specific combination ratio in the crystal and includes coordination water, lattice water, structure water, etc.

Preferable inorganic compounds having a water-keeping property for use in the present invention include, for example, calcium chloride, gold chloride, magnesium perchlorate, sodium perchlorate, germanium fluoride and vanadium chloride dioxide. Besides those mentioned above, the following inorganic compounds can be used in the present invention: silver perchlorate, aluminum chloride, aluminum iodide, boron triiodide, barium perchlorate, barium nitrate, beryllium chloride, bismuth chloride, calcium bromide, calcium iodide, cerium chloride, cobalt bromide, cesium chloride, iron bromide, iron iodide, gallium chloride, germanium iodide, iodine trichloride, indium chloride, iridium chloride, potassium sulfide, potassium selenite, potassium nitrite, potassium acetate, lanthanum chloride, lithium chloride, lithium chlorate, magnesium chloride, manganese chloride, molybdenum bromide, hydrazinium chloride, ammonium thiosulfate, sodium sulfide, sodium hexafluorophosphate, nickel bromide, phosphinic acid, palladium chloride dihydrate, rubidium hydroxide, ruthenium chloride, antimony chloride, selenium trioxide, strontium perchlorate, thorium chloride, titanium chloride, uranyl bromide, vanadium chloride, yttrium bromide and zinc bromide.

Organic compounds having a water-keeping property are those containing nitrogen, oxygen, phosphorus, sulfur, halogen, etc. therein and capable of forming hydrogen bonds with water molecules. Preferable organic compound having a water-keeping property include, for example, ethylene glycol, glycerol, N,N-dimethylhydrazine, 2-aminoethanol, 2-cyanopropionic acid and phenol-2,4-disulfonic acid. Besides those mentioned above, the following organic compounds can be used in the present invention: 2-bromoethanol, promazine hydrochloride, 2-naphthol-3,6-disulfonic acid, tropine, thiopental sodium, diethyl (R,R)-tantrate, trimethylamine oxide, N,N'-dimethylhydrazine, N,N'-dimethylthiourea, dimethylamine hydrochloride, ammonium acetate, methylhydrazine, N-methylhydroxylamine, 3-methoxy-1,2-propanediol and 4-amino-1,2,4-triazole.

Ion selective membrane can select a specific ion species. That is, it can selectively penetrate or induce only a specic ion species therethrough from a liquid sample also containing other ion species not destined for the measurement. The ion selective membrane must be water-insoluble, because a liquid sample is an aqueous solution, and can be either hydrophilic or hydrophobic so long as it is water-insoluble.

Such an ion selective membrane can be prepared in a known manner, for example, by dissolving an ion carrier and an organic binder into a solvent, applying the resulting solution to the surface of a water-insoluble salt layer, an electrolyte layer or a conductive layer, followed by drying. An ion carrier concentration is generally 0.05 to 10 g/m², and the thickness of ion selective membrane is preferably 10 to 500 μm.

Organic binder for use in the ion selective membrane can be natural or synthetic polymers capable of forming a thin film having a sufficient ion penetrability and an ion mobility together with an ionophore or an ionophore solvent and includes, for example, such known materials as poly(vinyl chloride), poly(vinyl alcohol), poly(vinylidone chloride), etc.

Ion carrier for use in the ion selective membrane can be substances capable of forming pairs with a desired specific alkali metal ion species, alkaline earth metal ion species, etc.

As a potassium ion carrier, such well known substances as valinomycin, cyclic polyether, etc. can be used. As a sodium ion carrier, such well known substances as monesin sodium, methylmonesin, etc. can be used. As materials for the ion selective membrane, such well known ion-exchangeable materials as quaternary borate, quaternary ammonium salts, etc. can be used.

It is desirable that the carrier solvent is sufficiently water-insoluble and non-volatile. Such well known substances as phthalate, sebacates, aromatic or aliphatic ethers, adipates, etc. are desirable ones.

Generally, the internal solid electrode is in such a structure that a metal is in contact with its insoluble salt, and can be shown by metal/metal salt, for example, by Ag/AgX, where X is a halogen such as Cl, Br, I, etc, which can be prepared by dipping a silver layer as a wire or plate into an aqueous solution of a halogen salt. As an insoluble salt, tetraphenylborate, tetraalkylborate or their derivative metal salts can be used.

The larger the thickness of the metal salt layer, the longer the time until an ion equilibrium is established between the metal salt layer and the intermediate layer. Thus, it is preferable that total thickness of the metal layer and the metal salt layer in the layer structure of metal/metal salt is not more than 500 μm and the thickness of the metal salt layer is 10 to 50% of that of the metal layer. It is not necessary that the entire surface of the metal layer is completely covered by the metal salt layer. That is, not more than 50% of the surface of the metal layer is preferably covered by the metal salt layer.

It is necessary that inorganic compounds having a water-keeping property are water-soluble and non-decomposable, and also that organic compounds having a water-keeping property are water-soluble and non-decomposable and have a low volatility. Particularly useful organic compounds are poly(alkylene oxide) having a molecular weight of 200 to 600, represented by the following chemical formula: $HO[(CH_2)_nO]_mH$, where m and $n \geq 1$, such as polyethyleneglycol, polymethyleneglycol, polypropyleneglycol, etc. having a vapor pressure of not more than 0.001 mm Hg (100° C.). These organic compounds have particularly a low volatility and thus a stable property of electrode can be maintained for a prolonged time.

The present invention will be described below, referring to specific examples using properly selected compounds from those mentioned above in comparison with the prior art.

Example 1

This example shows use of various organic compounds of low molecular weight having a water-keeping property and silver/silver chloride as an internal solid electrode.

FIG. 1 is a vertical cross-sectional view showing the structure of an ion sensor according to one embodiment of the present invention, where an ion selective membrane 4a is fixed along a liquid sample path 5 at the central position of an electrode body 1 and an intermediate layer 3a is sandwiched between an internal solid electrode 2a of silver/silver chloride and the ion selective membrane 4a, and a lead wire 11a is connected to the internal solid electrode 2a through the electrode body 1.

In this example, a voltage of about 0.7 V was applied between a concentrated nitric acid-treated silver plate (0.2 mm thick; 10 mm×10 mm square), as a positive electrode and a platinum wire (0.5 mm in diameter; 50 mm long) as a negative electrode for about 30 minutes in an aqueous 1 mM sodium chloride solution. After the voltage application the positive electrode was washed with water and dried, whereby a silver/silver chloride (Ag/AgCl) internal solid electrode was obtained. Then, about 10 μl of one of aqueous 5 mM KCl solutions prepared by adding 100 mg of poly-vinyl alcohol (PVA), 100 mg of potassium chloride and 100 mg of one of organic compounds having a water-keeping property given in Table 1 as Test Nos. 1 to 6 to 11 of water was dropwise applied to the AgCl surface of the internal solid electrode, and dried for about one day to form an intermediate layer on the internal solid electrode. The surface of the intermediate layer was then pasted with a potassium ion selective membrane having the following composition to prepare a potassium ion selective electrode.

The thus prepared electrode was connected to an external reference electrode through a salt bridge of saturated KCl, and subjected to potentiometry between the external reference electrode and the electrode, using an aqueous 100 mM potassium chloride solution as a test solution. Results of evaluation are given in Table 1. The entire electric battery for the potentiometry has the following general structure:

Ag/AgCl/saturated KCl/test solution as sample solution/ ion selective membrane/PVA-KCl-water-keeping material/ AgX/Ag, where X is Cl.

Composition of potassium ion selected membrane:

| | |
|---|---|
| Valinomycin | 0.1 g |
| Poly(vinyl chloride) | 2.0 g |
| Didodecyl phthalate | 0.01 g |

TABLE 1

| Test No. | Water-keeping material | Electrode sensitivity (mV/dec.) | Electrode resistance (M 75Ω) |
|---|---|---|---|
| 1 | Ethylene glycol | 56.1 | 75 |
| 2 | Glycerol | 56.3 | 42 |
| 3 | N,N-dimethyl hydrazine | 57.0 | 80 |
| 4 | 2-Aminoethanol | 56.6 | 95 |
| 5 | 2-Cyanopropionic acid | 57.1 | 67 |
| 6 | Phenol-2,4-disulfonic acid | 57.5 | 70 |
| 7 | None | 56.5 | 215 |

Electrode sensitivity to potassium ions was found to be about 56 to about 58 mV/dec. throughout all the test numbers, and the electrode resistance of the electrode without the water-keeping material (Test No. 7) was found to be 215 MΩ, whereas those of the electrodes with the water-keeping materials (Test Nos. 1 to 6) were found to be about a half to smaller fractions of that of Test No. 7. Decrease in the electrode resistance of the electrode with glycerol having a low volatility (Test No. 2) was particularly remarkable.

Example 2

This example shows use of various organic compounds (polymer compounds) having a water-keeping property and silver/silver chloride as an internal solid electrode.

9 electrodes were prepared in the same manner as in Example 1, except that the organic compounds having a water-keeping property of Example 1 were replaced with polymeric compounds as shown in Table 2 as Test Nos. 1 to 9, where polymethylene glycol (PMG), polyethylene glycol (PEG) and polypropylene glycol (PPG) each having molecular weights of 200, 400 and 600 were used. The same component ratio as in Table 1 was used for the preparation of the intermediate layer. The surfaces of the respective intermediate layers were then pasted with the same ion selective membrane as used in Example 1 to prepare potassium ion selective electrodes, which were subjected to the same potentiometry as in Example 1. Results of evaluation are given in Table 2.

TABLE 2

| Test No. | Water-keeping material | Electrode sensitivity (mV/dec.) | Electrode resistance (MΩ) |
| --- | --- | --- | --- |
| 1 | PMG-200 | 56.9 | 21 |
| 2 | PMG-400 | 56.2 | 22 |
| 3 | PMG-600 | 57.5 | 19 |
| 4 | PEG-200 | 57.6 | 18 |
| 5 | PEG-400 | 56.1 | 22 |
| 6 | PEG-600 | 57.2 | 18 |
| 7 | PPG-200 | 58.0 | 23 |
| 8 | PPG-400 | 57.3 | 19 |
| 9 | PPG-600 | 56.6 | 18 |
| 10 | None | 56.5 | 215 |

Electrode sensitivity to potassium ions was found to be about 56 to about 58 mV/dec throughout all the test numbers, as in Example 1, and the electrode resistance of the electrode without the water-keeping material (Test No. 10) was found to be 215 MG, whereas those of the electrodes with the water-keeping materials (Test Nos. 1 to 9) were found to be about one-tenth of that of Test No. 10. It seems that the polymeric compounds having a larger molecular weight have a particularly lower electrode resistance because of lower volatility.

Example 3

This example shows use of polyethylene glycol at various concentrations as a water-keeping material and silver/silver chloride as an internal solid electrode.

Silver/silver chloride internal solid electrodes were prepared in the same manner as in Example 1. Then, about 10 μl of one of aqueous 5 mM KCl solutions prepared by adding 100 mg of polyvinyl alcohol (PVA), 100 mg of potassium chloride (KCl) and polyethylene glycol (PEG) having a molecular weight of 600 in one of ratios of PEG to PVA by weight of 0.1, 0.5, 1.0, 2.0, 5.0 and 10.0 to 1 l of water was dropwise applied to the AgCl surface of silver/silver chloride (Ag/AgCl) internal solid electrode and dried for about one day to form an intermediate layer on the electrode. The thus obtained intermediate layers were then each pasted with the same ion selective membrane as used in Example 1 to form potassium ion selective electrodes, which were subjected to the same potentiometry as in Example 1. Results of evaluation are shown in Table 3.

TABLE 3

| Test No. | Ratio of PEG/PVA by weight | Electrode sensitivity (mV/dec.) | Electrode resistance (MΩ) |
| --- | --- | --- | --- |
| 1 | 0.1 | 56.3 | 51 |
| 2 | 0.5 | 57.3 | 21 |
| 3 | 1.0 | 56.0 | 19 |
| 4 | 2.0 | 56.8 | 18 |
| 5 | 5.0 | 57.9 | 18 |
| 6 | 10.0 | 57.2 | 17 |
| 7 | 0 | 56.5 | 215 |

Electrode sensitivity to potassium ions was found to be about 56 to about 58 mM/dec throughout all the test numbers, as in Example 1, and the electrode resistance of electrode without PEG (Test No. 7) was found to be 215 MΩ, whereas that of electrode with PEG in a ratio of 0.1 by weight (Test No. 1) was found to be as low as about 50 MΩ, and those of other electrodes with PEG in other ratios (Test Nos. 2 to 6) were found to be 21 MΩ or less, which was about one-tenth of that of Test No. 7.

Sodium ion selective electrodes and chloride ion selective electrodes could be prepared in the same manner as in Example 1, except that potassium chloride (KCl) was replaced with sodium chloride (NaCl) and sodium ion selective membranes and chloride ion selective membranes were used as ion selective membranes, and it was found that they could have similar properties of electrode to those of the potassium ion selective electrodes.

Example 4

This example shows use of polyethylene glycol at various concentrations as a water-keeping material and silver/silver bromide as internal solid electrodes.

Potassium ion selective electrodes were prepared in the same manner as in Example 3 by changing the internal solid electrodes of Example 3 to silver/silver bromide (Ag/AgBr) electrodes, preparing intermediate layers having the same compositions in Example 3 and pasting the surfaces of the intermediate layers with the same ion selective membrane as in Example 1 and subjected to the same potentiometry as in Example 1. Results of evaluation are shown in Table 4.

TABLE 4

| Test No. | Ratio of PEG to PVA by weight | Electrode sensitivity (mV/dec.) | Electrode resistance (MΩ) |
| --- | --- | --- | --- |
| 1 | 0.1 | 57.3 | 21 |
| 2 | 0.5 | 57.6 | 21 |
| 3 | 1.0 | 56.3 | 19 |
| 4 | 2.0 | 57.8 | 18 |
| 5 | 5.0 | 57.1 | 18 |
| 6 | 10.0 | 58.2 | 17 |
| 7 | 0 | 56.5 | 215 |

Electrode sensitivity to potassium ions was found to be about 56 to about 59 mV/dec throughout all the test numbers, and electrode resistance of electrode without PEG (Test No. 7) was found to be 215 MΩ, whereas those of electrodes with PEG in various ratios (Test Nos. 1 to 6) were found to be 21 MΩ or less, which was about one-fourth of that of Test No. 7. Judging only from the electrode resistance, silver/ silver bromide (Ag/AgBr) is better as internal solid electrode materials than silver/silver chloride (Ag/AgCl).

Example 5

This example shows use of various inorganic compounds having a water-keeping property and silver/silver chloride as internal solid electrodes.

Potassium ion selective electrodes were prepared in the same manner as in Example 1 except that the water-keeping materials were replaced with inorganic compounds i.e. calcium chloride ($CaCl_2 \cdot (H_2O)$), gold chloride ($AuCl_3 \cdot 2H_2O$), magnesium perchlorate ($Mg(ClO_4)_2 \cdot 8H_2O$), sodium perchlorate ($NaClO_4 \cdot (H_2O)$), germanium fluoride ($GeF_2$), and vanadium chloride dioxide ($VClO_2$), while using the same intermediate layer composition as used in Example 1 and then pasting the surfaces of the intermediate layers with the same ion selective membrane as used in Example 1, and then subjected to the same potentiometry as in Example 1. Results of evaluation are shown in Table 5.

TABLE 5

| Test No. | Water-keeping material | Electrode sensitivity (mV/dec.) | Electrode resistance (MΩ) |
|---|---|---|---|
| 1 | Calcium chloride | 57.2 | 22 |
| 2 | Gold chloride | 57.6 | 23 |
| 3 | Magnesium perchlorate | 57.3 | 18 |
| 4 | Sodium perchlorate | 56.8 | 20 |
| 5 | Germanium fluoride | 57.9 | 18 |
| 6 | Vanadium chloride dioxide | 57.2 | 20 |
| 7 | None | 56.8 | 215 |

Electrode sensitivity to potassium ions was found to be about 56 to about 58 mV/dec throughout all the test numbers, as in Example 1, and the electrode resistance without any water-keeping material (Test No. 7) was found to be 215 MΩ, whereas those of electrodes with the water-keeping materials (Test Nos. 1 to 6) were found to be about one-tenth of that of Test No. 7.

Example 6

This example shows use of calcium chloride having a water-keeping property at various concentrations and silver/ silver chloride as an internal solid electrode.

Potassium ion selective electrodes were prepared in the same manner as in Example 5, except that the water-keeping material was fixed to calcium chloride ($CaCl_2 1H_2O$) and intermediate layers were formed in various ratios of calcium chloride to PVA by weight, i.e. 0.1, 0.5, 1.0, 2.0, 5.0 and 10.0. The surfaces of intermediate layers were then pasted with the same ion selective membrane as used in Example 1. The potassium ion selective electrodes were subjected to the same potentiometry as in Example 1. Results of evaluation are shown in Table 6.

TABLE 6

| Test No. | Ratio of PEG to PVA by weight | Electrode sensitivity (mV/dec.) | Electrode resistance (MΩ) |
|---|---|---|---|
| 1 | 0.1 | 56.3 | 62 |
| 2 | 0.5 | 56.6 | 43 |

TABLE 6-continued

| Test No. | Ratio of PEG to PVA by weight | Electrode sensitivity (mV/dec.) | Electrode resistance (MΩ) |
|---|---|---|---|
| 3 | 1.0 | 56.5 | 21 |
| 4 | 2.0 | 58.8 | 19 |
| 5 | 5.0 | 57.9 | 17 |
| 6 | 10.0 | 58.2 | 17 |
| 7 | 0 | 56.5 | 215 |

Electrode sensitivity to potassium ions was found to be about 56 to about 59 mV/dec throughout all the test numbers, and the electrode resistance of electrode without the water-keeping material (Test No. 7) was found to be 215 MΩ, whereas those of electrodes in ratios of 0.1 and 0.5 by weight (Test Nos. 1 and 2) were found to be as low as about 60 MΩ and about 40 MΩ, respectively, and those of other electrodes (Test Nos. 3 to 6) were found to be 21 MΩ or less, which were about one-tenth of that of Test No. 7.

Example 7

This example shows use of calcium chloride having a water-keeping property at various concentrations and silver/ silver bromide as an internal solid electrode.

Potassium ion selective electrodes were prepared in the same manner as in Example 6 except that the internal solid electrode was replaced with silver/silver bromide (Ag/ AgBr). The same intermediate layer as disclosed in Example 6 was provided on each of the internal solid electrodes and then pasted with the same ion selective membrane as disclosed in Example 1 on the surface. The thus prepared potassium ion selective electrodes were subjected to the same potentiometry as in Example 1. Results of evaluation are shown in Table 7.

TABLE 7

| Test No. | Ratio to PVA by weight | Electrode sensitivity (mV/dec.) | Electrode resistance (MΩ) |
|---|---|---|---|
| 1 | 0.1 | 57.3 | 22 |
| 2 | 0.5 | 56.8 | 23 |
| 3 | 1.0 | 57.5 | 20 |
| 4 | 2.0 | 57.8 | 18 |
| 5 | 5.0 | 57.0 | 17 |
| 6 | 10.0 | 57.2 | 18 |
| 7 | 0 | 56.5 | 215 |

Electrode sensibility to potassium ions was found to be about 56 to about 58 mV/dec throughout all the test numbers, as in Example 1, and the electrode resistance of electrode without the water-keeping material (Test No. 7) was found to be 215 MΩ, whereas those of electrodes with the water-keeping material (Test Nos. 1 to 6) were found to be 23 MΩ or less, which was about one-tenth of that of Test No. 7. It was found that silver/silver bromide (Ag/AgBr) was better as internal solid electrode materials than silver/ silver chloride (Ag/AgCl), as in Example 4.

Example 8

This example shows use of polyethylene glycol at a constant concentration and calcium chloride at various concentration as water-keeping materials, and silver/silver chloride as an internal solid electrode.

Potassium ion selective electrodes were prepared in the same manner as in Example 6, except that polyethylene glycol (PEG) having a molecular weight of 600 and calcium chloride ($CaCl_2 \cdot 1H_2O$) were used as water-keeping materials, where a ratio of PEG to PVA by weight was set to 1.0, whereas that of calcium chloride to PVA was 0.1, 0.5, 1.0, 2.0, 5.0 and 10.0. The thus prepared intermediate layers on the internal solid electrodes were then each pasted with the same ion selective membrane as disclosed in Example 1. The thus prepared potassium ion selective electrodes were subjected to the same potentiometry as in Example 1. Results of evaluation are given in Table 8.

TABLE 8

| Test No. | Ratio to PVA by weight | | Electrode sensitivity (mV/dec.) | Electrode resistance (MΩ) |
| --- | --- | --- | --- | --- |
| | PEG600 | CaCl$_2$ | | |
| 1 | 1.0 | 0.1 | 56.4 | 22 |
| 2 | 1.0 | 0.5 | 57.6 | 23 |
| 3 | 1.0 | 1.0 | 58.5 | 20 |
| 4 | 1.0 | 2.0 | 57.8 | 19 |
| 5 | 1.0 | 5.0 | 57.1 | 18 |
| 6 | 1.0 | 10.0 | 58.1 | 17 |
| 7 | 0 | 0 | 56.5 | 215 |

Electrode sensitivity to potassium ions was found to be about 56 to about 59 mV/dec throughout all the test numbers, and the electrode resistance of the electrode without the water-keeping materials (Test No. 7) was found to be 215 MΩ, whereas those of electrodes with the water-keeping materials (Test Nos. 1 to 6) were found to be 23 MΩ or less, which was about one-tenth of that of Test No. 7.

Example 9

This example shows use of polyethylene glycol at a constant concentration and calcium chloride at various concentrations as water-keeping materials and silver/silver bromide as an internal solid electrode.

Potassium ion selective electrodes were prepared in the same manner as in Example 8, except that the internal solid electrode was replaced with silver/silver bromide (Ag/AgBr). Intermediate layers having the same compositions as in Example 8 on the internal solid electrodes were pasted with the same ion selective membrane as disclosed in Example 1. The thus prepared potassium ion selective electrodes were subjected to the same potentiometry as disclosed in Example 1. Results of evaluation are shown in Table 9.

TABLE 9

| Test No. | Ratio to PVA by weight | | Electrode sensitivity (mV/dec.) | Electrode resistance (MΩ) |
| --- | --- | --- | --- | --- |
| | PEG600 | CaCl$_2$ | | |
| 1 | 1.0 | 0.1 | 56.6 | 19 |
| 2 | 1.0 | 0.5 | 57.9 | 20 |
| 3 | 1.0 | 1.0 | 58.0 | 21 |
| 4 | 1.0 | 2.0 | 57.2 | 19 |
| 5 | 1.0 | 5.0 | 58.1 | 18 |
| 6 | 1.0 | 10.0 | 57.1 | 18 |
| 7 | 0 | 0 | 56.5 | 215 |

Electrode sensitivity to potassium ions was found to be about 56 to about 59 mV/dec. throughout all the test numbers, and the electrode resistance of the electrode without the water-keeping material (Test No. 7) was found to be 215 MΩ, whereas those of electrodes with the water-keeping materials (Test Nos. 1 to 6) were found to be 21 MΩ or less, which was about one-tenth of that of Test No. 7.

Example 10

This example shows evaluation of measurement accuracy when polyethylene glycol was used as a water-keeping material and silver/silver chloride was used as an internal solid electrode.

Potassium ion selective electrodes were prepared in the same manner as in Example 1, except that potassium chloride was replaced with polyethylene glycol (PEG) having a molecular weight of 600 as a water-keeping material for the intermediate layer, and subjected to measurement of potassium ion concentration in aqueous potassium chloride solutions having different potassium ion concentrations as test solutions (Test Nos. 1 to 3) to evaluate measurement accuracy and reproducibility. Results of evaluation are shown in Table 10.

TABLE 10

| Test No. | Potassium ion concentration (mM) | | Number of measurements | CV (%) |
| --- | --- | --- | --- | --- |
| | as prepared | Average of measurements | | |
| 1 | 1.5 | 1.49 | 20 | 0.22 |
| 2 | 2.0 | 2.02 | 20 | 0.31 |
| 3 | 3.0 | 3.01 | 20 | 0.16 |

It was found in the measurement of potassium chloride solutions at different potassium ion concentrations that covariance (CV) was kept within 1%, showing a good reproducibility.

Example 11

This example shows evaluation of measurement accuracy when calcium chloride was used as a water-keeping material and silver/silver chloride was used as an internal solid electrode.

Potassium ion selective electrodes were prepared in the same manner as in Example 1, except that potassium chloride was replaced with calcium chloride ($CaCl_2 \cdot 1H_2O$) as a water-keeping material for the intermediate layer, and subjected to measurement of potassium ion concentration in aqueous potassium chloride solutions having different potassium ion concentrations as test solutions (Test Nos. 1 to 3) to evaluate measurement accuracy and reproducibility. Results of evaluation are shown in Table 11.

TABLE 11

| Test No. | Potassium ion concentration (mM) | | Number of measurements | CV (%) |
| --- | --- | --- | --- | --- |
| | as prepared | Average of measurements | | |
| 1 | 1.5 | 1.48 | 20 | 0.28 |
| 2 | 2.0 | 2.04 | 20 | 0.33 |
| 3 | 3.0 | 3.03 | 20 | 0.19 |

It was found in the measurement of potassium chloride solutions at different potassium ion concentrations that covariance (CV) was kept within 1%, as in Example 10, showing a good reproducibility.

Figure 2:
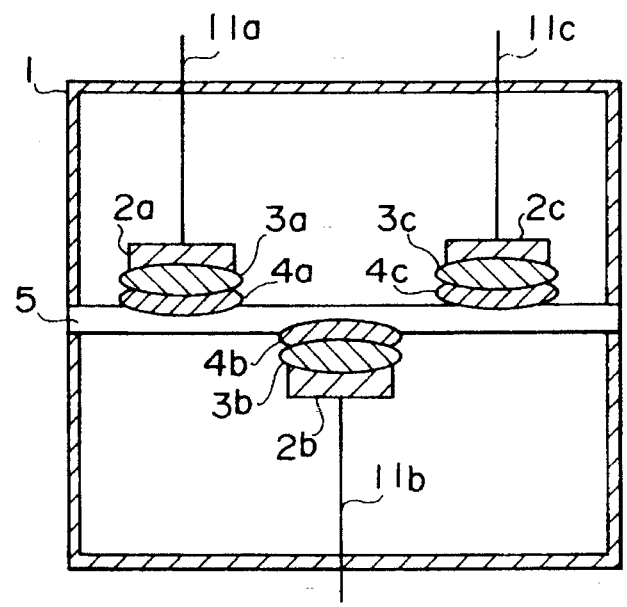
FIG. 2 is a vertical cross-sectional view showing the structure of an assembly of a plurality of ion sensors for measuring concentrations of a plurality of ion species according to another embodiment.

In the foregoing Example 1 to 11, description has been made of the structure of a single ion sensor for measuring concentrations of single ion species, but the present invention includes structures comprising a plurality of ion sensors, as shown in FIG. 2.

FIG. 2 is a vertical cross-sectional view showing the structure of an assembly of ion sensors for measuring concentrations of a plurality of ion species, which comprises internal solid electrodes 2a to 2c, intermediate layers 3a to 3c, ion selective membranes 4a to 4c and lead wires 11a to 11c. That is, a plurality of ion sensors are provided along a path through which a liquid sample flows and concentrations of a plurality of ion species are measured through contact of the individual ion selective membranes 4a to 4c of the ion sensors with a liquid sample.

Example 12

This example shows use of an ion sensitive field effect transistor.

In the following, description will be made of ion sensitive field effect transistors provided with the intermediate layer disclosed in one of the foregoing Example 1 to 11 and the following Example 29 to 32.

Figure 3:
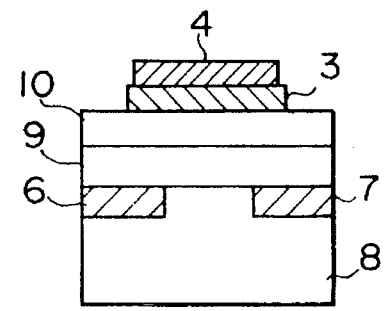
FIG. 3 is a vertical cross-sectional view showing the structure of an ion selective field effect transistor according to other embodiment of the present invention.

FIG. 3 is a vertical cross-sectional view showing the structure of a field effect transistor according to one embodiment of the present invention, where an n-type source 6 and an n-type drain 7 are formed on a silicon substrate 8, and covered with a $SiO_2$ membrane 9 and a $Si_3N_4$ insulation membrane 10, successively, to prepare a field effect transistor.

At first, a voltage of about 0.7 V was applied between a concentrated nitric acid-pretreated silver plate, 0.2 mm in thickness and 5 mm×5 mm square, as a positive electrode and a platinum wire, 0.5 mm in diameter and 50 mm long, as a negative electrode in an aqueous 1 mM NaCl solution for about 30 minutes. After the voltage application, the positive electrode was washed with water and dried to obtain a silver/silver chloride internal solid electrode. Then, the silver/silver chloride electrode was provided onto the $Si_3N_4$ insulation membrane 10. Then, an intermediate layer 3 having one of compositions disclosed in the foregoing Examples 1 to 11 and the following Examples 29 to 32 was formed on the AgCl surface of the internal solid electrode. For example, about 10 μl of an aqueous 5 mM KCl solution prepared by adding 100 mg of poly(vinyl alcohol) (PVA), 100 mg of potassium chloride (KCl) and 100 mg of polyethylene glycol (PEG) having a molecular weight of 600 to 1 l of water was dropwise applied to the AgCl surface of the internal solid electrode and dried for about one day.

Then, the surface of the intermediate layer 3 was pasted with a potassium ion selective membrane 4 having the same composition as disclosed in Example 1 to prepare a potassium ion sensitive field effect transistor. The thus prepared potassium ion sensitive field effect transistors were subjected to measurement of potassium ion concentrations in aqueous potassium chloride solutions having different potassium ion concentrations as test solutions (Test Nos. 1 to 3) to evaluate the measurement accuracy and reproducibility. Results of evaluation are shown in Table 12.

TABLE 12

| Test No. | Potassium ion concentration (mM) as prepared | Average of measurements | Number of measurements | CV (%) |
|---|---|---|---|---|
| 1 | 1.5 | 1.49 | 20 | 0.30 |
| 2 | 2.0 | 2.08 | 20 | 0.36 |
| 3 | 3.0 | 3.07 | 20 | 0.28 |

Sodium ion selective electrodes and chloride ion selective electrodes could be prepared in the same manner as in Example 12 by replacing potassium chloride (KCl) with sodium chloride (NaCl) as an inorganic salt constituent for the intermediate layer and using a sodium selective membrane and a chloride ion selective membrane, respectively, in place of the potassium ion selective membrane, and could have similar properties of electrode to those of the potassium ion selective electrodes.

Effects of the present invention will be described in detail below, referring to Examples according to embodiments of the present invention.

Example 13

This example shows comparison of the present ion selective electrodes with a conventional electrode in changes in electrode potential level in time course.

Figure 4:
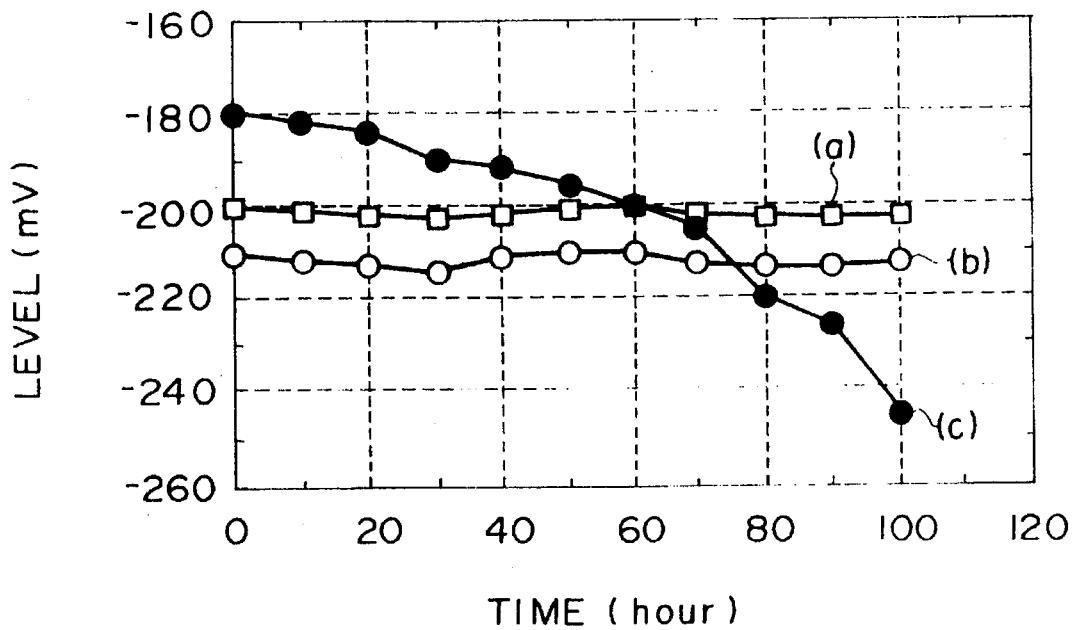
FIG. 4 is a diagram showing changes in the electrode potential level ion sensors in time course according to embodiments of the present invention and the conventional ion sensor.

FIG. 4 is a diagram showing changes in the electrode potential level in time course when the present ion selective electrodes and a conventional electrode were subjected as potassium ion measurement using an aqueous potassium chloride solution as a test solution, where electrode potential level values measured at every intervals of 2 hours were plotted for every ten hours.

In FIG. 4, curve (C) shows electrode potential level of the conventional electrode without any intermediate layer, which was prepared in the following manner: After first, a voltage of about 0.7 V was applied between a concentrated nitric acid-pretreated silver plate, 0.2 mm thick and 10 mm×10 mm square, as a positive electrode and a platinum wire, 0.5 mm in diameter and 50 mm long, as a negative electrode in an aqueous 1 mM KCl solution for about 30 minutes. After the voltage application, the positive electrode was washed with water and dried to obtain silver/silver chloride (Ag/AgCl) as an internal solid electrode. The thus obtained silver/silver chloride internal solid electrode was then pasted with a potassium ion selective membrane having the same composition as in Example 1 (as shown by 4a in FIG. 1) to prepare a potassium ion selective electrode.

In FIG. 4, curve (a) shows electrode potential level of the present potassium ion selective electrode with an intermediate layer containing polyethylene glycol (PEG) having a molecular weight of 600 as a water-keeping material in a ratio of PEG to poly(vinyl alcohol) (PVA) of 1.0 by weight, as shown in Example 3, and curve (b) shows electrode potential level of the present potassium ion selective electrode with an intermediate layer containing calcium chloride ($CaCl_2 \cdot 1H_2O$) as a water-keeping material in a ratio of calcium chloride to PVA of 1.0 by weight, as shown in Example 6.

In this example, results of measurements of changes in the electrode potential level in time course when these potassium ion selective electrodes were subjected to potassium ion measurement using an aqueous 100 mM potassium chloride solution as a test solution. It was found that the conventional potassium ion selective electrode had a considerable decrease in the electrode potential level in time course, as shown by curve (c) in FIG. 4, whereas the present potassium ion selective electrodes had no substantial decrease in the electrode potential level in time course, as shown by curves (a) and (b) in FIG. 4, which shows that a very stable equilibrium state between the ion selective membrane and the internal solid electrode could be maintained.

Example 14

This example shows comparison of the present ion selective electrodes with a conventional electrode in changes in drift of electrode potential level in time course.

Figure 5:
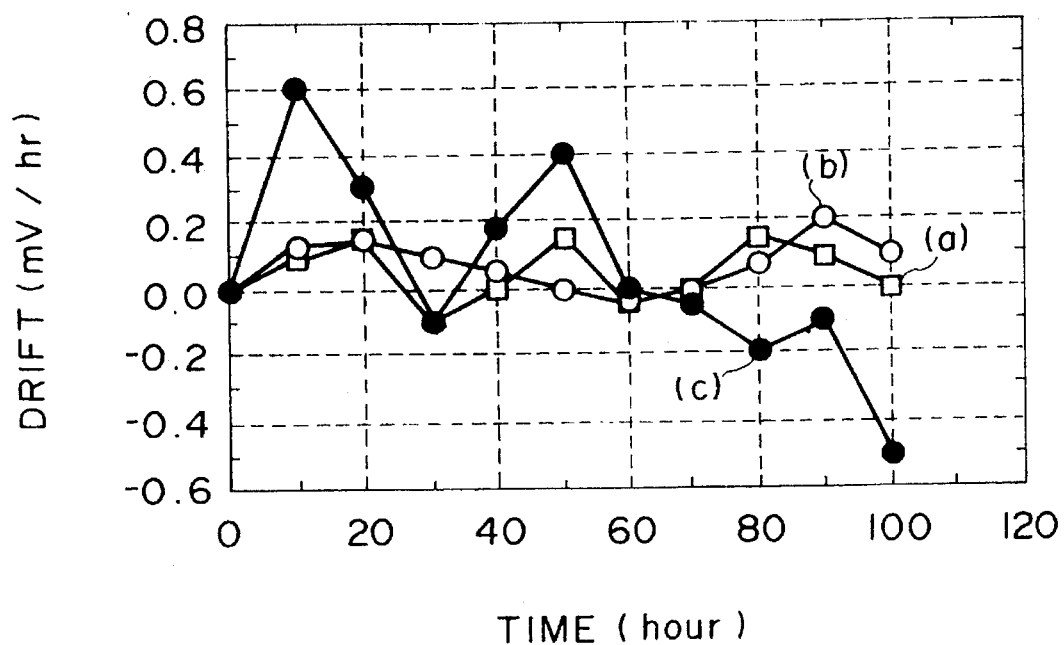
FIG. 5 is a diagram showing changes in the electrode potential level drift of ion sensors in time course according to other embodiments of the present invention and the conventional ion sensor.

FIG. 5 is a diagram showing changes in drift of electrode potential level in time course, when the present ion selective electrodes and a conventional electrode were subjected to potassium ion measurement using an aqueous potassium chloride solution as a test solution where from E(t) values, i.e. electrode potential level values measured at every intervals of 2 hours, a value of E(t+2)−E(t) was obtained as a drift, which was plotted for every 10 hours.

In FIG. 5, curve (c) shows changes in drift of electrode potential level of the conventional electrode without any intermediate layer, prepared in the same manner as in Example 13, in time course.

Course (a) shows changes in drift of electrode potential level of the present ion selective electrode with an intermediate layer containing polyethylene glycol (PEG) having a molecular weight of 600 as a water-keeping material in a ratio of PEG to poly(vinyl alcohol) (PVA) of 1.0 by weight, as shown in Example 3, in time curse and curve (b) shows changes in drift of electrode potential level of the present ion selective electrode with an intermediate layer containing calcium chloride (CaCl$_2$·1H$_2$O) as a water-keeping material in a ratio of calcium chloride to PVA of 1.0 by weight, as shown in Example 6, in time curse.

In this example, results of measurements of changes in the drift of electrode potential level in time course, when these potassium ion selective electrodes were subjected to potassium ion measurement using an aqueous 100 mM potassium chloride solution. It was found that the conventional ion selective electrode was rather unstable in the electrode potential level and had a large drift (curve (c) in FIG. 5 ), whereas the present ion selective electrodes were very stable in the drift over a prolonged time, as compared with the conventional electrode (curves (a) and (b) in FIG. 5).

As shown above, the present ion sensors are very practical, because good properties of electrode can be maintained for a prolonged time, as compared with the conventional one, and are particularly suitable for continuous measurement of liquid samples flowing along the path.

Example 15

This example shows use of various cyclic compounds having at least one double bond and containing at least one nitrogen atom as water-keeping materials and of silver/silver chloride as an internal solid electrode.

A silver/silver chloride internal solid electrode was prepared in the same manner as in Example 1 and then pasted with a potassium ion selective membrane having the following composition to prepare a conventional potassium ion selective electrode.

On the other hand, about 10 μl of an aqueous solution prepared by adding 100 mg of poly(vinyl alcohol) (PVA) and 100 mg of one of the following organic compound to 1 l of water was dropwise applied to the above-mentioned silver/silver chloride (Ag/AgCl) internal solid electrode, and dried for about one day to form an intermediate layer on the electrode. Then, the intermediate layer was then pasted with the above-mentioned potassium ion selective membrane having the following composition to prepare potassium ion selective electrodes according to the present invention. The organic compounds herein used were 2,4-pyridinediol (Chemical Formula 1), 4-pyridinemethanol (Chemical Formula 2), pyridine-3-carboxylic acid (Chemical Formula 3) and pyridine-2,5-carboxylic acid diethyl ether.

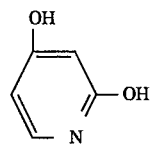

(Chemical Formula 1)

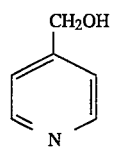

(Chemical Formula 2)

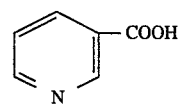

(Chemical Formula 3)

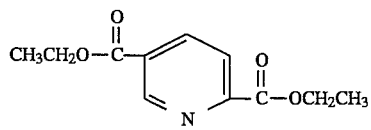

(Chemical Formula 4)

Then, an Ag/AgCl external reference electrode was connected with one of the thus prepared internal solid electrodes through a saturated KCl salt bridge to measure potential level differences between the external reference electrode and the internal solid electrode. That is, an electrode sensitivity, a potential level drift over 20 hours after the start of measurement and an electrode resistance were determined, using the same aqueous KCl solution as a test solution as in Example 1. Results of evaluation are given in Table 13, where Test Nos. 1 to 4 correspond to Chemical Formula 1 to 4, respectively. The entire battery for measuring a potential level difference with one of the potassium ion selective electrodes has the following structure:

Ag/AgCl/saturated KCl/test solution as liquid sample/ion selective membrane/PVA-organic compound/AgX/Ag where X is Cl.

Composition of potassium ion selective membrane:

| | |
|---|---|
| Valinomycin | 0.1 g |
| Poly(vinyl chloride) | 2.0 g |
| Didodecyl phthalate | 0.01 g |

TABLE 13

| Test No. | Electrode sensitivity (mV/dec.) | Potential level drift (mV/20 hr) | Electrode resistance (MΩ) |
|---|---|---|---|
| 1 | 56.2 | 8.9 | 23 |
| 2 | 57.2 | 10.2 | 22 |
| 3 | 56.6 | 7.6 | 20 |
| 4 | 57.3 | 6.5 | 19 |
| Conventional | 57.5 | 63 | 250 |

Electrode sensitivity to potassium ions was found to be about 56 to about 58 mV/dec. throughout all the test numbers including the conventional case, and electrode resistance of the conventional case was 250 MΩ, whereas those of Test Nos. 1 to 4 were found to be about one-tenth of that of the conventional case. It was also found that the potential level drift after 20 hours from the start of measurement of Test Nos. 1 to 4 was reduced to less than about one-fifth of that of the conventional case.

Example 16

This example shows use of various cyclic compounds having at least one double bond and containing at least one nitrogen atom as water-keeping materials and silver/silver bromide as an internal solid electrode.

Potassium ion selective electrodes were prepared in the same manner as in Example 15 except that the internal solid electrode was replaced with Ag/AgBr. That is, the same intermediate layer, ion selective membrane, preparation and measurement procedures and evaluation items as in Example 15 were employed. Results of evaluation are shown in Table 14, where water-keeping compounds used in Test Nos. 1 to 4 correspond to those of Chemical Formulas 1 to 4, respectively.

TABLE 14

| Test No. | Electrode sensitivity (mV/dec.) | Potential level drift (mV/20 hr) | Electrode resistance (MΩ) |
|---|---|---|---|
| 1 | 56.7 | 7.9 | 22 |
| 2 | 57.5 | 8.2 | 20 |
| 3 | 57.6 | 6.6 | 20 |
| 4 | 57.3 | 6.6 | 18 |
| Conventional | 57.1 | 56 | 120 |

Electrode sensitivity to potassium ions was found to be about 56 to about 58 mv/dec. throughout all the test numbers including the conventional case. It was found that the electrode resistivity of the conventional case was 120 MΩ, as in Example 15, whereas those of Test Nos. 1 to 4 were reduced to a few fractions of that of the conventional case. Potential level drift of Test Nos. 1 to 4 was reduced to less than one-fifth of that of the conventional case.

Example 17

This example shows use of various cyclic compounds having at least one double bond and containing at least one nitrogen atom as water-keeping materials and silver/silver iodide as an internal solid electrode.

Potassium ion selective electrodes were prepared in the same manner as in Example 15, except that the internal solid electrode was replaced with Ag/AgI. That is, the same intermediate layer, ion selective membrane, preparation and measurement procedures and evaluation items as in Example 15 were employed. Results of evaluation were given in Table 15, where water-keeping compounds used in Test Nos. 1 to 4 correspond to those of Chemical Formulas 1 to 4, respectively.

TABLE 15

| Test No. | Electrode sensitivity (mV/dec.) | Potential level drift (mV/20 hr) | Electrode resistance (MΩ) |
|---|---|---|---|
| 1 | 57.7 | 10.9 | 20 |
| 2 | 56.5 | 9.2 | 19 |
| 3 | 57.8 | 8.6 | 20 |
| 4 | 57.1 | 7.6 | 18 |
| Conventional | 57.0 | 51 | 105 |

Electrode sensitivity to potassium ions was found to be about 56 to about 58 mV/dec. throughout all the test numbers including the conventional case, as in Example 15. It was found that the electrode resistance of the conventional case was 105 MΩ, whereas those of Test Nos. 1 to 4 were reduced to a few fractions of that of the conventional case. Potential level drift was also found to be reduced to less than about one-fifth of that of the conventional case.

Example 18

This example shows use of various cyclic compounds having at least one double bond and at least one nitrogen atom as water-keeping materials, an inorganic salt and silver/silver chloride as an internal solid electrode.

Potassium ion selective electrodes were prepared in the same manner as in Example 15, except that an intermediate layer was formed from an aqueous solution prepared by adding 100 mg of poly(vinyl alcohol) (PVA), 100 mg of a cyclic compound selected from those mentioned in Example 15 as Chemical Formulas 1 to 4 and 100 mg of potassium chloride to 1 l of water on the surface of the internal solid electrode, where the surface of the intermediate layer was pasted with a potassium ion selective membrane having the same composition as in Example 15. The same evaluation items as in Example 15 were measured by potentiometry. Results of evaluation are shown in Table 16, where the water-keeping materials used in Test Nos. 1 to 4 correspond to those of Chemical Formulas 1 to 4.

The entire electric battery for the potentiometry had the following structure:

Ag/AgCl/saturated KCl/test solution as liquid sample/ion selective membrane/PVA-inorganic salt-cyclic compound/AgX/Ag, where X is Cl.

TABLE 16

| Test No. | Electrode sensitivity (mV/dec.) | Potential level drift (mV/20 hr) | Electrode resistance (MΩ) |
|---|---|---|---|
| 1 | 56.7 | 8.9 | 21 |
| 2 | 57.0 | 10.3 | 21 |
| 3 | 56.1 | 8.6 | 19 |
| 4 | 57.9 | 8.5 | 19 |
| Conventional | 57.1 | 41 | 220 |

Electrode sensitivity to potassium ions was found to be about 56 to about 58 mV/dec. throughout all the test numbers including the conventional case, as in Example 15. It was found that the electrode resistance of the conventional case was 220 MΩ, whereas those of Test Nos. 1 to 4 were reduced to 2 MΩ or less, which was about one-tenth of that of the conventional case. Potential level drift was found to be reduced to about one-fourth of that of the conventional case.

Example 19

This example shows use of various cyclic compounds having at least one double bond and containing at least one nitrogen atom as water-keeping materials, an inorganic salt and silver/silver bromide as an internal solid electrode.

Potassium ion selective electrodes were prepared in the same manner as in Example 18 except that the internal solid electrode was replaced with silver/silver bromide (Ag/AgBr). The same intermediate layer, ion selective membrane, preparation and measurement procedures and evaluation items as in Example 18 were employed. Results of evaluation are shown in Table 17, where the water-keeping materials used in Test Nos. 1 to correspond to those of Chemical Formula 1 to 4, respectively.

TABLE 17

| Test No. | Electrode sensitivity (mV/dec.) | Potential level drift (mV/20 hr) | Electrode resistance (MΩ) |
| --- | --- | --- | --- |
| 1 | 55.7 | 6.9 | 20 |
| 2 | 56.5 | 7.2 | 20 |
| 3 | 55.6 | 6.8 | 20 |
| 4 | 57.1 | 7.6 | 19 |
| Conventional | 56.1 | 35 | 110 |

Electrode sensitivity to potassium ions of Test Nos. 1 to 4 including the conventional case was found to be about 56 to about 58 mV/dec, as in Example 15. It was found that the electrode resistance of the conventional case was 110 MΩ, whereas those of Test Nos. 1 to 4 were reduced to about one-fifth of that of the conventional case. Potential level drift of Test Nos. 1 to 4 was found to be less than about one-fourth of that of the conventional case.

Example 20

This example shows use of various cyclic compounds having at least one double bond and containing at least one nitrogen atom as water-keeping material, an inorganic salt and silver/silver iodide as an internal solid electrode.

Potassium ion selective electrodes were prepared in the same manner as in Example 18, except that the internal solid electrode was replaced with silver/silver iodide. The same intermediate layer, ion selective membrane, preparation and measurement procedures and evaluation items as in Example 18 were employed. Results of evaluation are shown in Table 18, where the water-keeping material used in Test Nos. 1 to 4 correspond to those of Chemical Formulas 1 to 4, respectively.

TABLE 18

| Test No. | Electrode sensitivity (mV/dec.) | Potential level drift (mV/20 hr) | Electrode resistance (MΩ) |
| --- | --- | --- | --- |
| 1 | 58.5 | 8.9 | 21 |

TABLE 18-continued

| Test No. | Electrode sensitivity (mV/dec.) | Potential level drift (mV/20 hr) | Electrode resistance (MΩ) |
| --- | --- | --- | --- |
| 2 | 58.2 | 9.3 | 18 |
| 3 | 56.5 | 7.6 | 20 |
| 4 | 57.5 | 7.9 | 19 |
| Conventional | 57.2 | 43 | 100 |

Electrode sensitivity to potassium ions of Test Nos. 1 to 4 including the conventional case was found to be about 56 to about 59 mV/dec. It was found that the electrode resistance of the conventional case was 100 MΩ, whereas those of Test Nos. 1 to 4 were reduced to about one-fifth of that of the conventional case. Potential level drift was found to be less than about one-fourth of that of the conventional case.

Example 21

This example shows use of pyridine -2,5-carboxylic acid diethyl ether at various concentrations as a water-keeping material and silver/silver chloride as an internal solid electrode.

Potassium ion selective electrodes were prepared in the same manner as in Example 15, except that only pyridine-2,5-carboxylic acid diethyl ether of Chemical Formula 4 was used in ratios of 0.1, 0.5, 1.0, 2.0 and 5.0 to PVA by weight in Test Nos. 1 to 5, respectively, as a water-keeping material for the intermediate layer. The same internal solid electrode, ion selective membrane, preparation and measurement procedures and evaluation items as in Example 15 were employed. Results of evaluation are shown in Table 19.

TABLE 19

| Test No. | Ratio to PVA by weight | Electrode sensitivity (mV/dec.) | Potential level drift (mV/20 hr) | Electrode resistance (MΩ) |
| --- | --- | --- | --- | --- |
| 1 | 0.1 | 57.7 | 25.2 | 52 |
| 2 | 0.5 | 57.3 | 25.0 | 31 |
| 3 | 1.0 | 58.1 | 9.6 | 19 |
| 4 | 2.0 | 57.1 | 10.5 | 19 |
| 5 | 5.0 | 56.9 | 11.2 | 20 |
| Conventional | — | 57.1 | 51 | 220 |

Electrode sensitivity to potassium ions was found to be about 56 to about 59 mV/dec. throughout all the test numbers including the conventional case. Electrode resistance of the conventional case was found to be 220 MΩ, whereas it was found that those of Test No. 1 (ratio to PVA:0.1 by weight) and Test No. 2 (ratio to PVA:0.5 by weight) were reduced to about 50 and about 30 MΩ, respectively, and those of other test numbers were reduced to 20 MΩ or less, which was about one-tenth of that of the conventional case. Potential level drifts of Test Nos. 1 and 2 were found to be a little as large as about 25 mV/2 hr, but those of other test numbers were reduced to less than about one-fifth of that of the conventional case.

Example 22

This example shows use of pyridine-3-carboxylic acid at various concentrations as a water-keeping material and silver/silver chloride as an internal solid electrode.

Potassium ion selective electrodes were prepared in the same manner as in Example 15, except that only pyridine-3-carboxylic acid of Chemical Formula 3 was used in ratios to PVA of 0.1, 0.5, 1.0, 2.0 and 5.0 by weight as a water-keeping material for the intermediate layer. The same internal solid electrode, ion selective membrane, preparation and measurement procedures and evaluation items as in Example 15 were employed. Results of evaluation are shown in Table 20.

TABLE 20

| Test No. | Ratio to PVA by weight | Electrode sensitivity (mV/dec.) | Potential level drift (mV/20 hr) | Electrode resistance (MΩ) |
|---|---|---|---|---|
| 1 | 0.1 | 58.7 | 23.2 | 50 |
| 2 | 0.5 | 56.3 | 9.0 | 21 |
| 3 | 1.0 | 58.5 | 9.2 | 20 |
| 4 | 2.0 | 58.1 | 10.1 | 19 |
| 5 | 5.0 | 57.9 | 11.6 | 21 |
| Conventional | — | 57.2 | 40 | 215 |

Electrode sensitivity to potassium ions was found to be about 56 to about 59 mV/dec. throughout all the test numbers including the conventional case. Electrode resistance of the conventional case was found to be 215 MΩ, whereas that of Test No. 1 (ratio:0.1 by weight) was reduced to 50 MΩ, and those of Test Nos. 2 to 4 were reduced to 21 MΩ or less, which was about one-fourth of that of the conventional case. Potential level drift of Test No. 1 (ratio:0.1 by weight) was a little as high as about 23 mV/20 hr, and those of Test Nos. 2 to 4 were reduced to about one-fourth of that of the conventional case.

Example 23

This example shows use of pyridine-2,5-carboxylic acid diethyl ether as a water-keeping material, an inorganic salt at various concentrations and silver/silver chloride as an internal solid electrode.

Potassium ion selective electrodes were prepared in the same manner as in Example 15, except that only pyridine-2,5-carboxylic acid diethyl ether of Chemical Formula 4 was used in a ratio to PVA of 1.0 by weight as a water-keeping organic compound for the intermediate layer and potassium chloride was used as an inorganic salt in ratios to PVA of 0.1, 0.5, 1.0, 2.0 and 5.0 by weight (Test Nos. 1 to 5, respectively). The same internal solid electrode, ion selective membrane, preparation and measurement procedures and evaluation items as Example 15 were employed. Results of evaluation are shown in Table 21.

TABLE 21

| Test No. | Ratio to PVA by weight | Electrode sensitivity (mV/dec.) | Potential level drift (mV/20 hr) | Electrode resistance (MΩ) |
|---|---|---|---|---|
| 1 | 0.1 | 57.2 | 11.2 | 22 |
| 2 | 0.5 | 58.3 | 9.0 | 21 |
| 3 | 1.0 | 58.8 | 9.2 | 19 |
| 4 | 2.0 | 57.9 | 9.5 | 19 |
| 5 | 5.0 | 58.9 | 9.2 | 19 |
| Conventional | — | 57.4 | 45 | 220 |

Electrode sensitivity to potassium ions was found to be about 56 to about 59 mV/dec. throughout all the test numbers including the conventional case. Electrode resistance of Test Nos. 1 to 5 was reduced to 22 MΩ or less, which was about one-tenth of that of the conventional case, irrespective of ratios of potassium chloride to PVA. Potential level drift of Test Nos. 1 to 5 was also reduced to about one-fourth of that of the conventional case, irrespective of ratios of potassium chloride to PVA.

Example 24

This example shows evaluation of reproducibility when pyridine-2,5-carboxylic acid diethyl ether was used as a water-keeping material and silver/silver chloride was used as an internal solid electrode.

Potassium ion selective electrodes were prepared in the same manner as in Example 15, except that only pyridine-2,5-carboxylic acid diethyl ether of Chemical Formula 4 was used as a water-keeping organic compound for the intermediate layer. The same internal solid electrode, ion selective membrane, intermediate layer composition and preparation method as in Example 15 were employed. The thus prepared electrodes were subjected to determination of reproducibility, using aqueous potassium chloride solutions having different potassium ion concentrations (Test Nos. 1 to 3) as test solutions. Results of evaluation are shown in Table 22.

TABLE 22

| Test No. | Potassium ion concentration (mM) as prepared | Average of measurements | Number of measurements | CV (%) |
|---|---|---|---|---|
| 1 | 1.5 | 1.49 | 20 | 0.22 |
| 2 | 2.0 | 2.02 | 20 | 0.31 |
| 3 | 3.0 | 3.01 | 20 | 0.16 |

CV values were kept within 1% in the measurement of the aqueous potassium chloride solutions having different potassium ion concentration, showing a good reproducibility.

Example 25

This examples shows evaluation of reproducibility when pyridine-2,5-carboxylic acid diethyl ether as a water-keeping material, an inorganic salt and silver/silver chloride as an internal solid electrode were used.

Potassium ion selective electrodes were prepared in the same manner as in Example 18, except that pyridine-2,5-carboxylic acid diethyl ether of Chemical Formula 4 as a water-keeping organic compound and potassium chloride as an inorganic salt were used each in a ratio to PVA of 1.0 by weight to prepare an intermediate layer, and subjected to determination of reproducibility, using aqueous potassium chloride solutions having different potassium ion concentrations (Test Nos. 1 to 3) as test solutions. The same internal solid electrode, ion selective membrane and preparation and measurement procedures as in Example 18 were employed. Results of evaluation are shown in Table 23.

TABLE 23

| Test No. | Potassium ion concentration (mM) as prepared | Average of measurements | Number of measurements | CV (%) |
|---|---|---|---|---|
| 1 | 1.5 | 1.48 | 20 | 0.28 |
| 2 | 2.0 | 2.04 | 20 | 0.33 |
| 3 | 3.0 | 3.03 | 20 | 0.19 |

CV values were kept within 1% in the measurement of the aqueous potassium chloride solutions having different potassium ion concentrations, showing a good reproducibility, as in Example 24.

In the foregoing Examples 12, 15 to 24, description has been made of the structure of a single ion sensor for measuring a concentration of single ion specis, but the present invention includes structures comprising a plurality of ion sensors, an shown in FIG. 2.

Example 26

This example shows evaluation of reproducibility of field effect transistors.

Potassium ion sensitive, field effect transistors were prepared in the same manner as in Example 12, using one of the intermediate layers disclosed in Examples 15 to 25, and subjected to determination of reproducibility, using aqueous potassium chloride solutions having different potassium ion concentrations (Test Nos. 1 to 3) as test solutions. Results of evaluation are shown in Table 24.

TABLE 24

| Test No. | Potassium ion concentration (mM) as prepared | Average of measurements | Number of measurements | CV (%) |
|---|---|---|---|---|
| 1 | 1.5 | 1.49 | 20 | 0.30 |
| 2 | 2.0 | 2.08 | 20 | 0.36 |
| 3 | 3.0 | 3.07 | 20 | 0.28 |

CV values were kept within 1% in the measurement of aqueous potassium chloride solutions having different potassium ion concentrations, showing a good reproducibility.

Sodium ion selective electrodes and chloride ion selective electrodes could be prepared in the same manner as in Example 12 by replacing potassium chloride (KCl) with sodium chloride (NaCl) as an inorganic salt constituent for the intermediate layer and using a sodium selective membrane and chloride ion selective membrane, respectively, in place of the potassium ion selective membrane, and could have similar properties of electrode to those of the potassium ion selective electrodes.

Example 27

This example shows comparison of the present ion selective electrodes with a conventional one in changes in the electrode potential level in time course.

Figure 6:
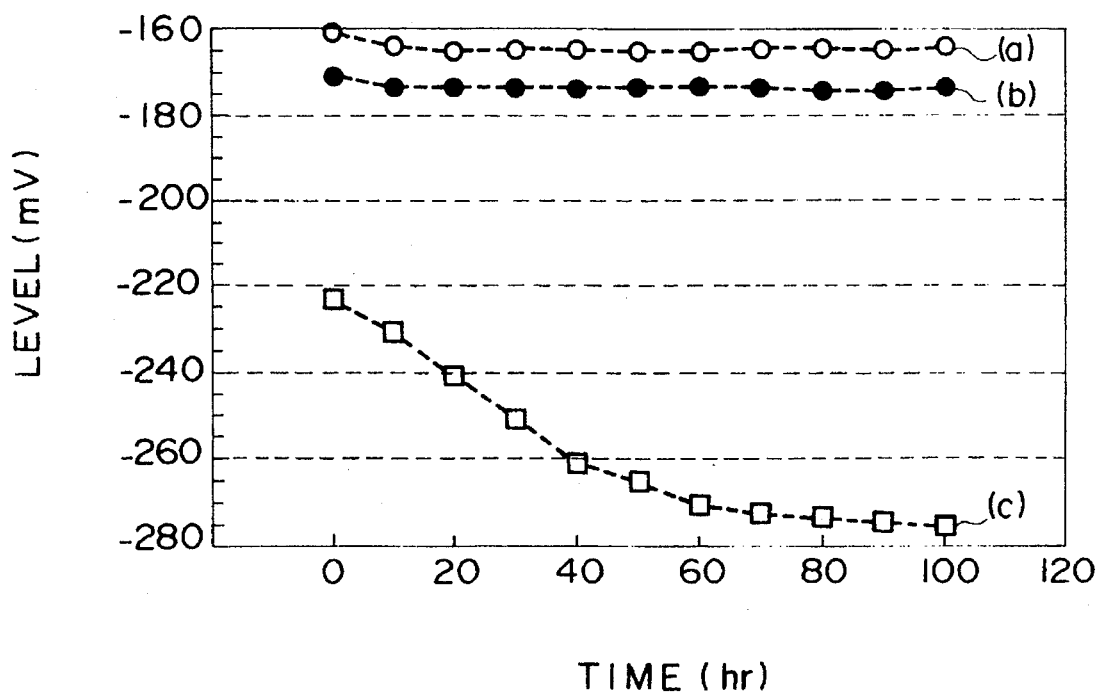
FIG. 6 is a diagram showing changes in the electrode potential level of ion sensors in time course according to further embodiments of the present invention and the conventional ion sensor.

FIG. 6 is a diagram showing changes in the electrode potential level in time course when the present ion selective electrodes and a conventional one, as used in Example 15, were subjected to potassium ion measurement of an aqueous potassium chloride solution as a test solution, where results of electrode potential level measured at every intervals of 2 hours were plotted for every ten hours.

In FIG. 6, curve (c) shows changes in the electrode potential level of the conventional electrode without any intermediate layer, prepared in the same manner as in Example 15, in time course, when subjected to potassium ion measurement of an aqueous 100 mM potassium chloride solution as a test solution.

Curve (a) shows changes in the electrode potential level of an ion selective electrode of the present invention with an intermediate layer containing a water-keeping organic compound of Chemical Formula 1, prepared in the same manner as in Example 15, in time course, and curve (b) shows those of another ion selective electrode of the present invention with an intermediate layer containing a water-keeping organic compound of Chemical Formula 3, prepared in the same manner as in Example 15, in time course.

The conventional ion selective electrode had a considerable decrease in the electrode potential level in time course, whereas the present ion selective electrodes had no substantial decrease in the electrode potential level in time course. This shows that a very stable equilibrium state was maintained between the ion selective membrane and the internal solid electrode of the present ion selective electrodes for a prolonged time.

Example 28

This example shows comparison of the present ion selective electrodes with a conventional one in changes in the electrode potential level in time course.

Figure 7:
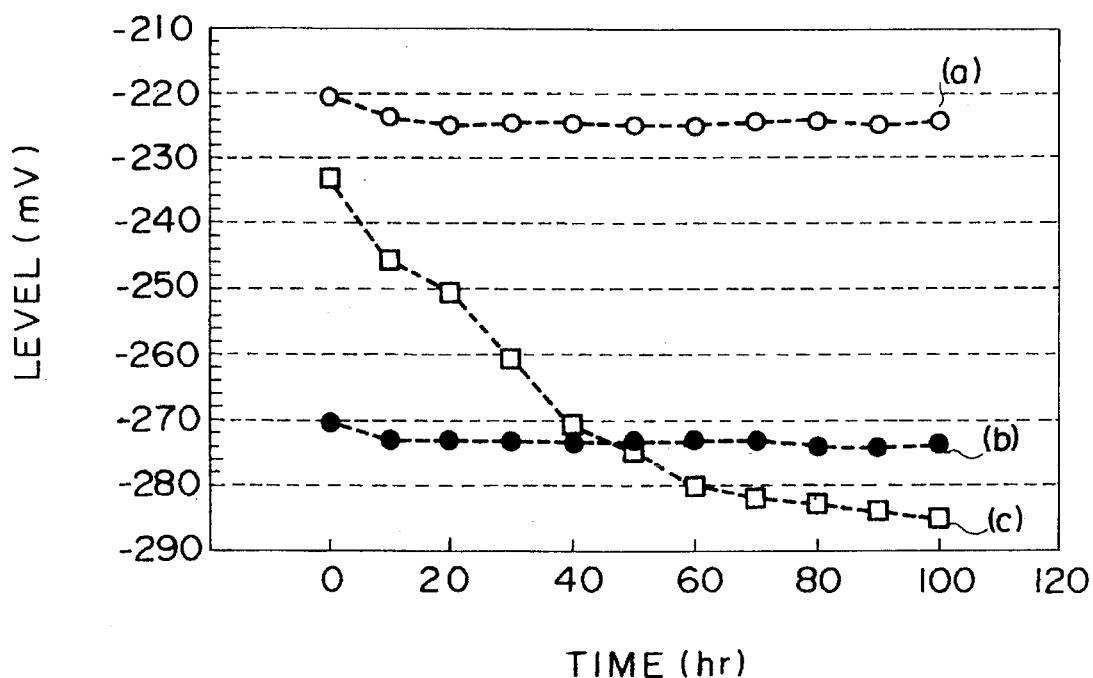
FIG. 7 is a diagram showing changes in the electrode potential level of ion sensors in time course according to still further embodiments of the present invention and the conventional ion sensor.

FIG. 7 is a diagram showing changes in the electrode potential level in time course when the present ion selective electrodes, as used in Example 18, and a conventional electrode having the same composition as shown in Example 15, were subjected t potassium ion measurement of an aqueous potassium chloride solution as a test solution.

In FIG. 7, curve (c) shows changes in the electrode potential level of the conventional electrode without any intermediate layer, prepared in the same manner as in Example 15, in time course, when subjected to potassium ion measurement of an aqueous 100 mM potassium chloride solution as a test solution.

Curve (a) shows changes in the electrode potential level of an ion selective electrode of the present invention with an intermediate layer containing a water-keeping organic compound of Chemical Formula 2, prepared in the same manner as in Example 18, in time course and curve (b) shows those of another ion selective electrode of the present invention with an intermediate layer containing a water-keeping organic compound of Chemical Formula 4, prepared in the same manner as in Example 18, in time course.

The conventional ion selective electrode was rather unstable in changes in the electrode potential level in time course, showing a high drift, whereas the present ion selective electrodes were very stable in changes in the electrode potential level in time course, showing a less drift for a prolonged time than that of the conventional electrode.

That is, the present ion sensor can have stable properties of electrode for a long time, as compared with the conventional one, and thus is more practical, and is particularly suitable for continuous measurement of liquid samples flowing along the path.

Example 29

This example shows use of polyethylene gylcols having various molecular weights as a water-keeping material and silver/silver chloride as an internal solid electrode.

Five potassium ion selective electrodes each with one of the following intermediate layers were prepared in the same manner as in Example 2, where intermediate layers containing one of polyethylene glycol (PEG) having a molecular weight of 200, 400, or 600 as water-keeping materials each in one of ratios of PEG to PVA of 0.1, 1.0, 2.0 and 5.0 by weight were employed. Intermediate layers containing one of PEGs in a ratio of PEG to PVA of 10.0 by weight were not practically available because mixed aqueous solutions containing one of PEGs and PVA were unstable and soon were separated into two phases, i.e. polyethylene glycol phase and water phase. Each of the surfaces of these intermediate layers was pasted with the same ion selective membrane as in Example 1 to prepare potassium ion selective electrodes, which were subjected to measurement of changes in the electrode potential level in time course, using an aqueous 100 mM potassium chloride solution. Averages of drifts of electrode potential level of 5 electrodes for each molecular weight of PEGs for the time from the start of potential level measurement to 20 hours thereafter are shown in Table 25.

TABLE 25

| Test No. | Water-keeping material | Potential level drift (mV/20 hr) Ratio to PVA by weight | | | |
| --- | --- | --- | --- | --- | --- |
| | | 0.1 (wt. %) | 1.0 (wt. %) | 2.0 (wt. %) | 5.0 (wt. %) |
| 1 | PEG200 | 12.3 | 10.2 | 9.0 | 13.5 |
| 2 | PEG400 | 10.5 | 8.8 | 7.2 | 11.3 |
| 3 | PEG600 | 12.0 | 8.1 | 5.0 | 12.1 |

Potassium ion selective electrode with an intermediate layer containing PEG600 (molecular weight: 600) in a ratio to PVA of 2.0 by weight was found to have a minimum potential level drift.

Example 30

This example shows use of an inorganic salt at various concentrations, polyethylene glycol as a water-keeping material and silver/silver chloride as an internal solid electrode.

Five potassium ion selective electrodes each with one of the following intermediate layers were prepared in the same manner as in Example 2, where intermediate layers containing PEG600 (molecular weight: 600) as a water-keeping material and potassium chloride as an inorganic salt in one of ratios of KCl to PVA of 0.001, 0.01, 0.1, 1.0 and 2.0 by weight were employed. Each of the surfaces of these intermediate layers was then pasted with the same ion selective membrane as in Example 1 to prepare potassium ion selective electrodes, which were subjected to measurement of changes in the electrode potential level in time course, using an aqueous 100 mM potassium chloride solution. Averages of drifts of electrode potential level of 5 electrodes for each KCl ratio for the time from the start of potential level measurement to 20 hours thereafter are shown in Table 26.

TABLE 26

| Ratio to PVA by weight (wt. %) | 0.001 | 0.01 | 0.1 | 1.0 | 2.0 |
| --- | --- | --- | --- | --- | --- |
| Potential level | 45.3 | 31.3 | 9.2 | 9.0 | 10.5 |

TABLE 26-continued drift (mV/20 hr)

Below a ratio of KCl to PVA of 0.01 by weight, the potential level drift was considerably large, whereas in ratios of 0.1, 1.0 and 2.0 by weight the potential level drift was small and there were no substantial difference in the drift therebetween.

Example 31

This example shows use of polyethylene glycols having various molecular weights or ethylene glycol as water-keeping materials and silver/silver chloride as an internal solid electrode.

Figure 8:
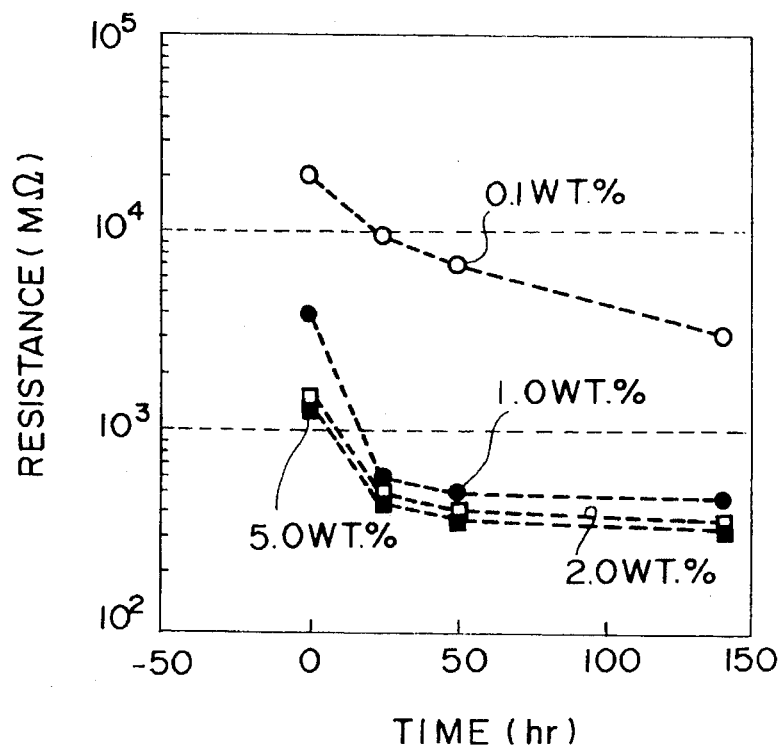
FIGS. 8 to 11 are diagrams showing changes in the electrode resistance of ion sensors in time course according to still further embodiments of the present invention.
Figure 9:
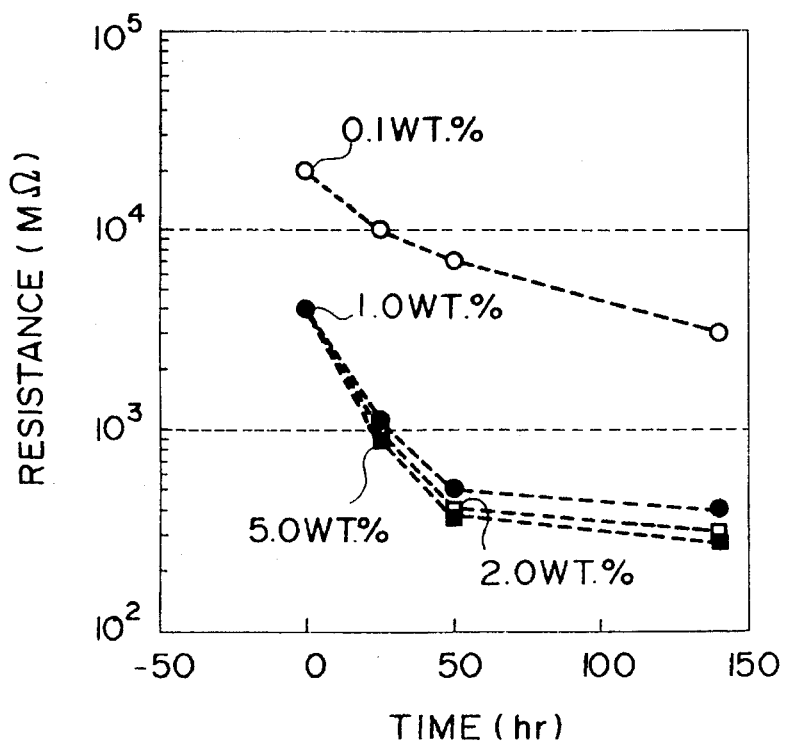
Figure 10:
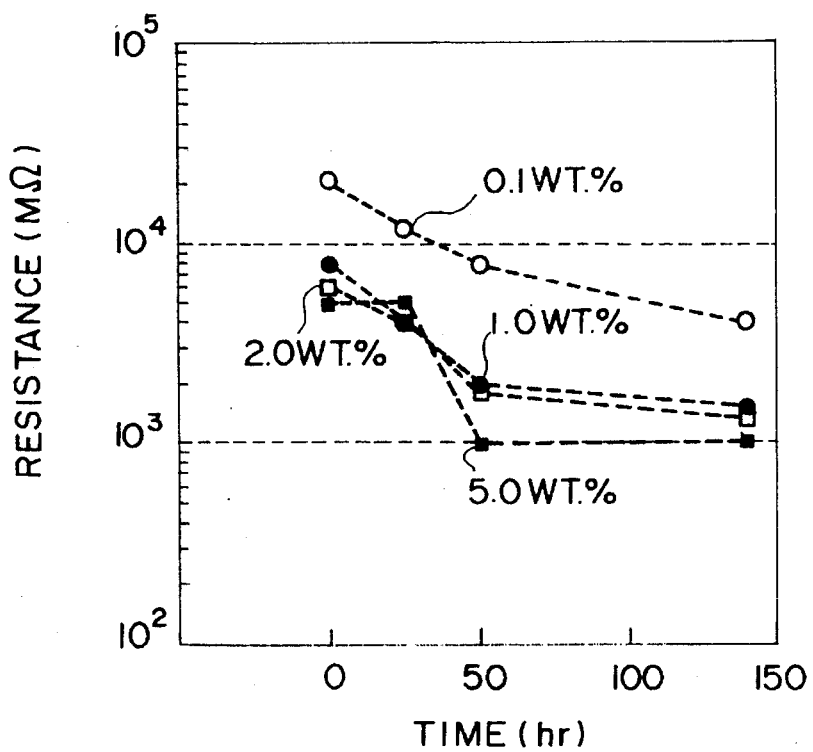
Figure 11:
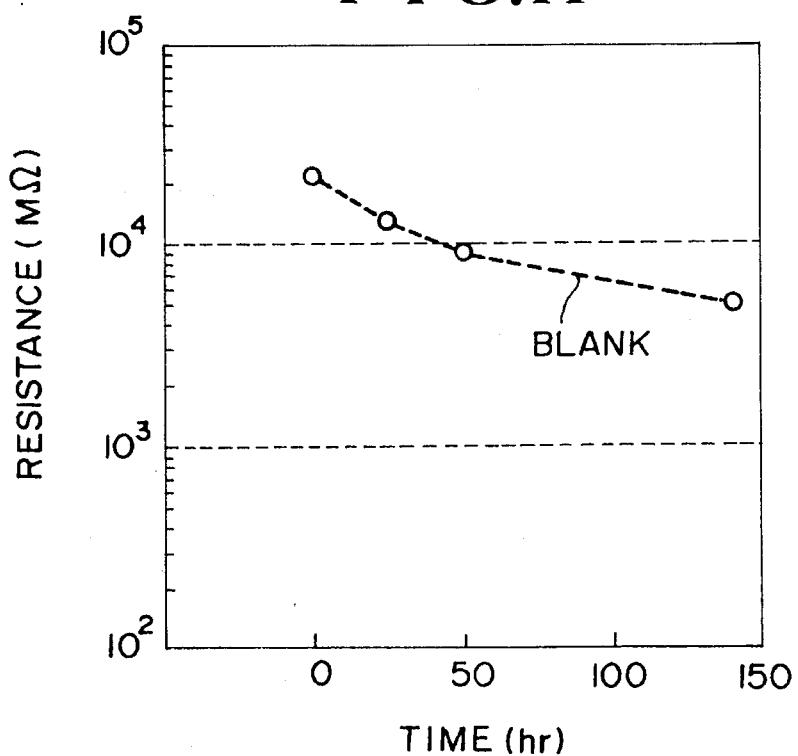

Chloride ion selective electrodes were prepared in the same manner as in Example 2, except that potassium chloride was replaced with sodium chloride, and a chloride ion selective membrane was used as an ion selective membrane, where one of intermediate layers containing ethylene glycol or polyethylene glycol (PEG) having a molecular weight of 200 or 600 in one of ratios to PVA of 0.1, 2.0 and 5.0 by weight was used. At the same time, a chloride ion selective electrode with an intermediate layer composed only of PVA without any water-keeping material was prepared in the same manner as above to obtain reference data (blank data). An intermediate layer having a ratio of PEG to PVA of 10.0 by weight was not practically available, because an mixed aqueous solution of PEG and PVA was unstable and was soon separated into two phases, i.e. polyethylene glycol phase and water phase. Changes in the electrode resistance in time course were measured when the chloride ion selective electrodes were dipped in an aqueous 100 mM sodium chloride solution as a liquid sample in the same manner as in Example 2. Results of evaluations are shown in FIGS. 8 to 11, where FIGS. 8, 9 and 10 show results of evaluation when polyethylene glycol having a molecular weight of 200, polyethylene glycol having a molecular weight of 600 and ethylene glycol were used as water-keeping materials, respectively, and FIG. 11 shows blank data without using any water-keeping material.

Electrodes with an intermediate layer having one of the water-keeping materials in a ratio of 0.1 by weight and the electrode with an intermediate layer containing no water-keeping material had no considerable decrease in the electrode resistance when dipped in the aqueous sodium chloride solution, whereas electrodes with an intermediate layer containing PEG having a molecular weight of 200 or 600 in ratios of 1.0, 2.0 and 5.0 by weight had a considerable decrease in the electrode resistance, whereby an effect of the water-keeping materials was confirmed.

Example 32

This example shows use of polyethylene glycol as a water-keeping material, an inorganic salt at various concentrations and silver/silver chloride as an internal solid electrode.

Five chloride ion selective electrodes each with one of the following intermediate layers were prepared in the same manner as in Example 2, except that sodium chloride was used as an inorganic salt, where polyethylene glycol (PEG) having a molecular weight of 600 was used as a water-keeping material for the intermediate layers in ratio to PVA of 2.0 by weight and sodium chloride was used as an inorganic salt in one of ratios to PVA of 0.01, 0.11 1.0 and 2.0 by weight. The surfaces of the intermediate layers were then pasted with the same chloride ion selective electrode as in Example 31 to prepare chloride ion selective electrodes, which were subjected to measurement of changes in the electrode potential level in the same aqueous sodium chloride solution as in Example 31. Averages of drifts of electrode potential level of 5 electrodes for each NaCl ratio for the time from the start of potential level measurement to 20 hours thereafter are shown n Table 27.

TABLE 27

| Ratio to PVA by weight (wt. %) | 0.01 | 0.1 | 1.0 | 2.0 |
|---|---|---|---|---|
| Potential level drift (mV/20 hr) | 35.3 | 10.2 | 8.0 | 9.5 |

In a ratio of NaCl to PVA of 0.01 by weight the potential level drift was considerably large, whereas in ratios of 0.1, 1.0 and 2.0 by weight the potential level drift was so small that there was no considerable differences therebetween.

What is claimed is:

1. An ion sensor having an ion selectivity, which comprises an internal solid electrode of metal/metal salt, comprising of an electroconductive layer of at least one metal and a layer of an insoluble salt of the metal in contact with the electroconductive layer, an ion selective membrane whose supporting membrane comprises a hydrophobic polymer, and an intermediate layer which keeps water molecules, provided between the internal solid electrode and the ion selective membrane, the intermediate layer comprises of dried residues of an aqueous solution comprising an inorganic compound having a water-keeping property or an organic compound having a water-keeping property, a hydrophilic polymer and an inorganic salt.

2. An ion sensor according to claim 1, where the inorganic compound is an inorganic salt having water of crystallization.

3. An ion sensor according to claim 2, wherein the inorganic salt is calcium chloride, gold chloride, magnesium perchlorate, magnesium fluoride or vanadium chloride dioxide.

4. An ion sensor according to claim 1, wherein the organic compound forms a hydrogen bond with water molecules.

5. An ion sensor according to claim 4, wherein the organic compound has a characteristic group of nitroso, sulfonic acid, alcohol or hydrazine.

6. An ion sensor according to claim 5, wherein the organic compound is selected from the group consisting of ethylene glycol, glycerol, N,N-dimethylhydrazine, 2-aminoethanol, 2-cyanopropionic acid and phenol-2,4-disulfonic acid.

7. An ion sensor according to claim 1, wherein the organic compound is a poly(alkyl oxide) having a molecular weight of 200 to 600, represented by the following chemical formula:

wherein n and m are each $\geq 1$.

8. An ion sensor according to claim 7, wherein the poly(alkyl oxide) is selected from the group consisting of polymethylene glycol, polyethylene glycol and polypropylene glycol.

9. An ion sensor according to claim 1, wherein the inorganic salt has a concentration in terms of a ratio to the hydrophilic polymer of 0.1 to 2 by weight and the organic compound having a water-keeping property has a concentration in terms of a ratio to the hydrophilic polymer of 0.1 to 5 by weight.

10. An ion sensor according to claim 1, wherein the inorganic compound having a water-keeping property has a concentration in terms of a ratio to the hydrophilic polymer of 0.1 to 10 by weight.

11. An ion sensor according to claim 1, wherein the hydrophilic polymer is poly(vinyl alcohol) and the organic compound having a water-keeping property is a poly(alkyl oxide) having a molecular weight of 200 to 600.

12. An ion sensor according to claim 11, wherein the hydrophilic polymer is poly(vinyl alcohol) and the organic compound having a water-keeping property is polyethylene glycol having a molecular weight of 600.

13. An ion sensor having an ion selectivity, which comprises an internal solid electrode of metal/metal salt, comprising of an electroconductive layer of at least one metal and a layer of an insoluble salt of the metal in contact with the electroconductive layer, an ion selective membrane whose supporting membrane comprises a hydrophobic polymer, and an intermediate layer which keeps water molecules, provided between the internal solid electrode and the ion selective membrane, the intermediate layer comprises dried residues of an aqueous solution comprising a mixture of a hydrophilic polymer, an inorganic salt, an inorganic compound having a water-keeping property and an organic compound having a water-keeping property.

14. An ion sensor according to claim 13, wherein the inorganic salt has a concentration in terms of a ratio to the hydrophilic polymer of 0.1 to 2 by weight and the organic compound having a water-keeping property has a concentration in terms of a ratio to the hydrophilic polymer of 0.1 to 5 by weight.

15. An ion sensor according to claim 13, wherein the inorganic compound having a water-keeping property has a concentration in terms of a ratio to the hydrophilic polymer of 0.1 to 10 by weight.

16. An ion sensor according to claim 13, wherein the hydrophilic polymer is poly(vinyl alcohol) and the organic compound having a water-keeping property is poly(alkyl oxide) having a molecular weight of 200 to 600.

17. An ion sensor according to claim 13, wherein the hydrophilic polymer is poly(vinyl alcohol) and the organic compound having a water-keeping property is polyethylene glycol having a molecular weight of 600.

18. An ion sensor according to claim 13, wherein the inorganic salt is calcium chloride, gold chloride, magnesium perchlorate, magnesium fluoride or vanadium chloride dioxide.

19. An ion sensor according to claim 16, wherein the poly(alkyl oxide) is selected from the group consisting of polyethylene glycol, polyethylene glycol and polypropylene glycol.

20. An ion sensor having an ion selectivity, which comprises an internal solid electrode of metal/metal salt, comprising an electroconductive layer of at least one metal and a layer of an insoluble salt of the metal in contact with the electroconductive layer, an ion selective membrane whose supporting membrane comprises a hydrophobic polymer, and an intermediate layer which keeps water molecules, provided between the internal solid electrode and the ion selective membrane, the intermediate layer comprises dried residues of an aqueous solution comprising an inorganic compound having a water-keeping property or an organic compound having a water-keeping property, a hydrophilic polymer and an inorganic salt, where the organic compound having a water-keeping property is selected from the group consisting of polymethylene glycol, polyethylene glycol and polypropylene glycol and has a molecular weight of 200 to 600, and the inorganic compound having a water-keeping property is selected from the group consisting of calcium chloride, gold chloride, magnesium perchlorate, magnesium fluoride and vanadium chloride dioxide.

21. An ion sensor having an ion selectivity, which comprises an internal solid electrode of metal/metal salt, comprising an electroconductive layer of at least one metal and a layer of an insoluble salt of the metal in contact with the electroconductive layer, an ion selective membrane whose supporting membrane comprises a hydrophobic polymer, and an intermediate layer which keeps water-molecules, provided between the internal solid electrode and the ion selective membrane, the intermediate layer comprises dried residues of an aqueous solution comprising a hydrophilic polymer, an inorganic salt and a polymer of hydrazine derivative represented by the following chemical formula:

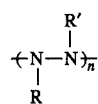

where R and R' are hydrogen atoms, alkyl groups or hydroxyl groups and n>1.

22. An ion sensor having an ion selectivity, which comprises an internal solid electrode of metal/metal salt, comprising an electroconductive layer of at least one metal and a layer of an insoluble salt of the metal in contact with the electroconductive layer, an ion selective membrane whose supporting membrane comprises a hydrophobic polymer, and an intermediate layer which keeps water molecules, provided between the internal solid electrode and the ion selective membrane, the intermediate layer comprises dried residues of an aqueous solution comprising a chain compound or a cyclic compound having at least one double bond and containing at least one nitrogen atom, and a hydrophilic polymer.

23. An ion sensor according to claim 22, wherein the chain compound or the cyclic compound is pyridine, pyridazine, pyrazine, s-triazine, quinoline, isoquinoline, isoquinoline, quinoxaline, acridine or a derivative thereof.

24. An ion sensor according to claim 22, wherein the intermediate layer further contains an inorganic salt, selected from the group consisting of calcium chloride, gold chloride, magnesium perchlorate, magnesium fluoride and vanadium chloride dioxide.

25. An ion sensor according to claim 24, wherein the chain compound or the cyclic compound and the inorganic salt are each in a ratio to the hydrophilic polymer of 1 to 5% by weight.

26. An ion sensor according to claim 22, wherein the intermediate layer further contains an inorganic salt selected from the group consisting of calcium chloride, gold chloride, magnesium perchlorate, magnesium fluoride and vanadium chloride dioxide, and the chain compound or the cyclic compound is pyridine, pyridazine, pyrazine, s-triazine, quinoline, isoquinoline, isoquinoline, quinoxaline, acridive or a derivative thereof.

27. An ion sensor according to any one of claims 1, 13, 20, 21 and 22, wherein the insoluble salt of the internal solid electrode has an anion selected from the group consisting of halide ion, tetraphenylborate ion, tetraphenylborate derivative ion, tetraalkylborate ion and tetraalkylborate derivative ion.

28. An ion sensor according to any one of claims 1, 13, 20, 21 and 22, wherein the hydrophilic polymer is selected from the group consisting of poly(vinyl alcohol), polyethylene oxide, polypropylene oxide, polyacrylic acid salt, polymethacrylic acid salt, polystyrene sulfonic acid salt, carboxymethyl cellulose and a derivative thereof.

29. An ion sensor according to any one of claims 1, 13, 20, 21 and 22, wherein a plurality of the ion sensors are provided along a path through which a liquid sample is passed, where the ion selective membranes of the respective ion sensors are in contact with the liquid sample.

30. An ion sensitive field effect transistor, which comprises a substrate, source and drain formed on the substrate, an insulation membrane covering the sources and the drains, and an ion selective membrane whose supporting membrane comprises a hydrophobic polymer, and an intermediate layer provided between the insulation membrane and the ion selective membrane, the intermediate layer comprises dried residues of one of an aqueous solution comprising an inorganic compound having a water-keeping property or an organic compound having a water-keeping property, a hydrophilic polymer and an inorganic salt; an aqueous solution comprising a mixture of a hydrophilic polymer, an inorganic salt, an inorganic compound having a water-keeping property and an organic compound having a water-keeping property; an aqueous solution comprising an inorganic compound having a water-keeping property or an organic compound having a water-keeping property, a hydrophilic polymer and an inorganic salt, where the organic compound having a water-keeping property is selected from the group consisting of polymethylene glycol, polyethylene glycol and polypropylene glycol and has a molecular weight of 200 to 600, and the inorganic compound having a water-keeping property is selected from the group consisting of calcium chloride, gold chloride, magnesium perchlorate, magnesium fluoride and vanadium chloride dioxide; an aqueous solution comprising a hydrophilic polymer, an inorganic salt and a polymer of hydrazine derivative represented by the following chemical formula:

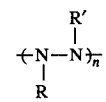

where R and R' are hydrogen atoms, alkyl groups or hydroxyl groups and n≧1; and an aqueous solution comprising a chain compound or a cylic compound having at least one double bond and containing at least one nitrogen atom and a hydrophilic polymer.

* * * * *